United States Patent
Giancola

(10) Patent No.: US 11,986,222 B2
(45) Date of Patent: May 21, 2024

(54) DEVICE FOR THE SELECTIVE BIOLOGICAL SYNTHESIS OF A BONE TISSUE

(71) Applicant: Rinaldo Giancola, Milan (IT)

(72) Inventor: Rinaldo Giancola, Milan (IT)

(*) Notice: Subject to any disclaimer, the term of this patent is extended or adjusted under 35 U.S.C. 154(b) by 367 days.

(21) Appl. No.: 17/556,336

(22) Filed: Dec. 20, 2021

(65) Prior Publication Data
US 2023/0190339 A1  Jun. 22, 2023

(51) Int. Cl.
*A61B 17/70* (2006.01)
*A61B 17/86* (2006.01)

(52) U.S. Cl.
CPC ........ *A61B 17/7098* (2013.01); *A61B 17/864* (2013.01)

(58) Field of Classification Search
CPC ... A61B 17/7098; A61B 17/684; A61B 17/86; A61B 17/84
See application file for complete search history.

(56) References Cited

U.S. PATENT DOCUMENTS 6,048,343 A    4/2000  Mathis et al.

FOREIGN PATENT DOCUMENTS

| DE | 20317120 U1 | 4/2004 | |
| EP | 2582312 B1 | 8/2017 | |
| WO | 2009063524 A2 | 5/2009 | |
| WO | WO-2011158193 A1 * | 12/2011 | ......... A61B 17/7098 |
| WO | WO-2019072355 A1 * | 4/2019 | ......... A61B 17/8605 |

* cited by examiner

*Primary Examiner* — Kevin T Truong
*Assistant Examiner* — Diana Jones
(74) *Attorney, Agent, or Firm* — Tutunjian & Bitetto, P.C.

(57) ABSTRACT

The present invention relates to a device for the selective biological synthesis of a bone tissue arranged to allow the stabilization of a fracture or an osteoporotic bone tissue and for the introduction of medicinal substances for bone diseases.

13 Claims, 2 Drawing Sheets

DEVICE FOR THE SELECTIVE BIOLOGICAL SYNTHESIS OF A BONE TISSUE

TECHNICAL FIELD OF THE INVENTION

The present invention relates to a device for the selective biological synthesis of a bone tissue, and the introduction of medicinal substances for bone diseases.

STATE OF THE PRIOR ART

In the field of orthopedics, in particular of traumatology, some devices are known which allow, through the injection of bone cement and osteoconductive, osteoinductive and medicament substances in the intervention site, to stabilize any bone fractures generated by a trauma or an osteoporotic tissue, especially in elderly female patients, particularly affected by this condition. Indeed, for these patients, the low level of bone stability does not guarantee satisfactory results of stabilization with traditional means of osteosynthesis.

Thus, for example, the application published under number WO2009063524A2 describes a screw for the stabilization of a bone fracture, comprising a hollow longitudinal body equipped, in its lateral surface, with through holes through which the passage of bone cement or other active substances that can be introduced through the head of the screw itself is allowed.

The U.S. Pat. No. 6,048,343 presents a system of bone screws which includes a cannulated screw, equipped with openings, and an adapter suitable to be coupled reversibly to the screw and to means for the injection of bone cement or of a suitable composition.

However, these systems have the disadvantage that the fluids introduced into the screw, due to the physical laws that regulate their passage, flow through the holes closest to the inlet, making it difficult to reach the furthest holes, especially in the case of high viscosity fluids, such as bone cement. For this reason, the stabilization of fractures or porous bone tissue is made difficult and not entirely effective through the use of such known devices.

The German utility model DE20317120U1 discloses a bone screw, in particular a pedicle screw, having a threaded shank equipped with a through opening in the longitudinal direction for the introduction of a guide wire, the screw also includes a predisposition to fix at least partially an insertable stiffening device in the opening.

The European patent EP2582312B1, on the other hand, teaches a device for the selective biological synthesis of a bone tissue having a screw internally defining a longitudinal channel where a stem can be inserted which can be constrained internally to the screw by means of a screwing engagement at the rear of the screw itself.

This solution does not show satisfactory properties in terms of stability to deformation and resistance to shear forces.

SUMMARY OF THE INVENTION

An object of the present invention is to provide a new device for the selective biological synthesis and for the introduction of medicinal substances for bone diseases (osteoporosis, tumors, infections, etc.).

Another object of the present invention is to provide a device as aforesaid which guarantees greater stability to deformation and greater resistance to shear forces than the solutions proposed so far, thereby obtaining with a cannulated screw the mechanical strength of a solid screw, therefore allowing an early resumption of the load after the procedure.

Another object of the present invention is to provide a device which is capable of effectively preventing the reflux of biological fluids or other fluids into the cannulated screw.

Another object of the present invention is to provide a device for the selective biological synthesis of a bone tissue, which ensures to reinforce the bone tissue present at the insertion site waiting its eventual regeneration and/or consolidation.

According to an aspect of the present invention, these objects are solved by a device for the selective biological synthesis of a bone tissue as specified in the present application.

The present application refers to preferred and advantageous embodiments of the invention.

BRIEF DESCRIPTION OF THE DRAWINGS

Other features and advantages of the invention will be more evident from the description of an embodiment of a device for selective biological synthesis, illustrated by way of example in the accompanying drawings in which.

In the accompanying drawings, identical parts or components are indicated by the same reference numbers.

DETAILED DESCRIPTION OF THE INVENTION

Figure 1:
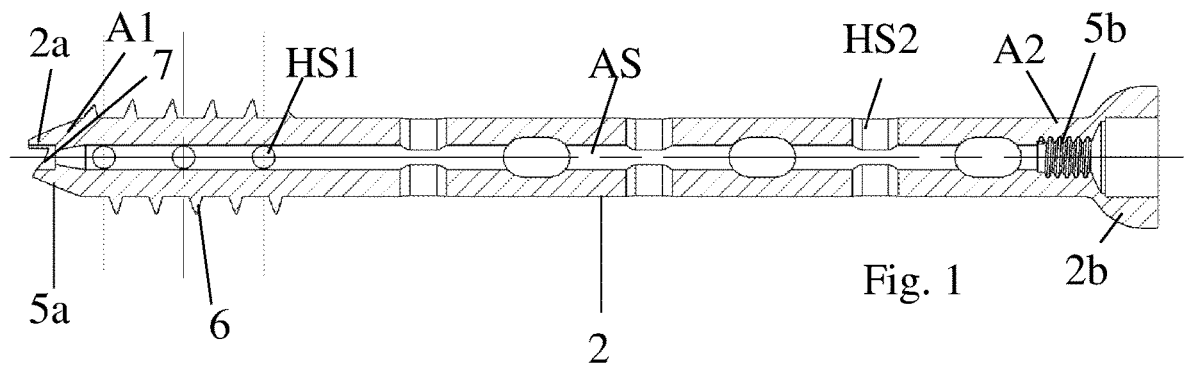
FIG. 1 is a cross-section view of a cannulated screw for a device according to the present invention.
Figure 2:
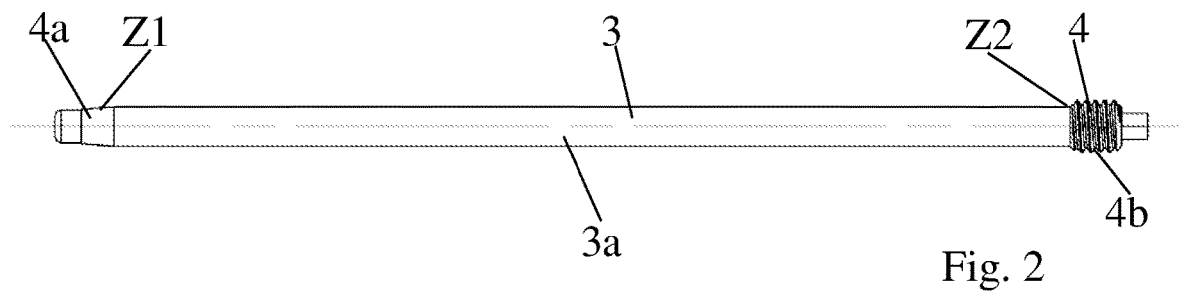
FIGS. 2 and 3 are side and perspective views, respectively, of a stem or pin for a device according to the present invention.
Figure 3:
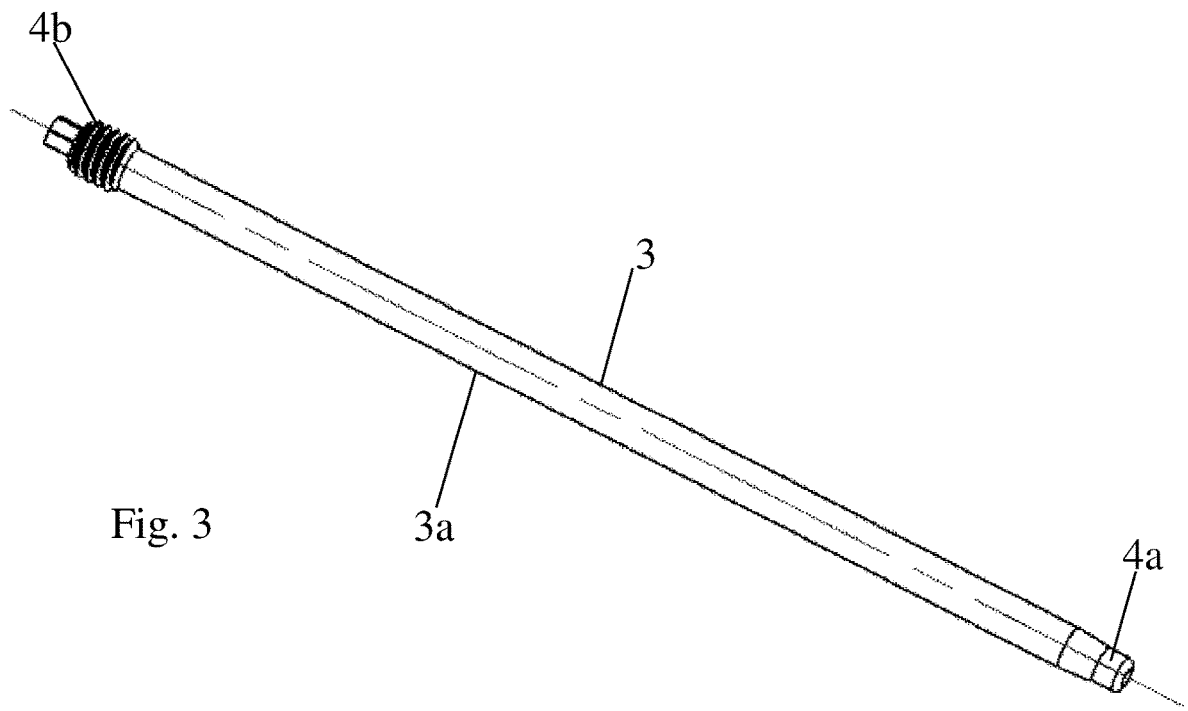

With reference first of all to FIGS. 1 to 3, a device 1 for the selective biological synthesis of a bone tissue and for the introduction of medicinal substances for bone diseases (osteoporosis, tumors, infections, etc.) arranged to allow the stabilization of a fracture F or an osteoporotic bone tissue B has been illustrated, which device 1 includes a graft tubular component or cannulated screw 2 defining a axial channel or seat AS as well as at least one hole or slot HS1, HS2 transversal to the axial seat AS or better to the main extension axis of the same, which extends from the back 2b to the tip 2a of the tubular component or cannulated screw 2. If desired, a plurality of holes or slots HS1, HS2 transversal to the axial seat AS distributed along the length of the cannulated screw 2 is provided, i.e. each obtained at a respective cross section of screw 2.

The hole/s or slot/s HS1, HS2 is/are in fluid communication with the axial seat AS.

Clearly, the device is biocompatible with the tissue in which it is inserted.

Preferably, the graft tubular component or cannulated screw 2 has a substantially rectilinear extension.

The device 1 is then provided with a stem or pin 3 which can be housed or inserted into the axial through seat AS, which stem or pin 3 has first removable engagement means 4a, 4b externally to the stem or pin 3 or better to the respective main body 3a, while the cannulated screw 2 comprises second removable engagement means 5a, 5b in the axial seat AS designed to removably engage the first engagement means 4a, 4b.

Preferably, the stem or pin 3 has a substantially straight development.

By "removable engagement" according to the present invention it is to be meant means in general ensuring to engage in a stable, but removable and therefore releasable manner, although this may no longer be necessary or possible after implantation of the device, even for the possible insertion of biological fluids or not that could interfere with the engagement means.

More specifically, the first engagement means 4a, 4b extend at at least two zones Z1, Z2 of the stem or pin 3 at a distance from each other, while the second engagement means 5a, 5b extend at at least two areas A1, A2 of the cannulated screw 2 at a distance from each other equal to the distance between the two zones of the first engagement means 4a, 4b, so that the first engagement means 4a, 4b engage or can engage at each extension zone Z1, Z2 a respective extension area A1, A2 of the second engagement means 5a, 5b.

Basically, when the stem or pin 3 is in position within the graft tubular component or cannulated screw 2, a simultaneous engagement by the first engagement means 4a, 4b of several extension areas A1, A2 suitably spaced apart of the second engagement means 5a, 5b, with an extension zone Z1, Z2 of the first means in engagement with a respective extension area A1, A2 of the second engagement means is obtained.

This ensures that starting from a cannulated screw the mechanical strength of a full screw is obtained, which allows a patient to obtain the original functional performance, such as, in particular, loading again in a short time after surgery.

Advantageously, the two zones Z1, Z2 are at a distance from each other equal to at least half the length of the stem or pin 3 and, even more advantageously, at a distance from each other equal to at least 70% or 80% or 90% of the length of the stem or pin 3.

The at least two areas A1, A2 of the cannulated screw 2 are, as indicated above, at a distance between them equal to the distance between the two zones Z1, Z2 of the first engagement means 4a, 4b. Preferably, the two areas A1, A2 are one at the front end or tip 2a of the cannulated screw 2 and the other at the rear end or back 2b of the cannulated screw 2.

Naturally, the first engagement means 4a, 4b will extend for a respective section of the stem or pin 3 (which is for example between 1/60 and 1/4, for example between 3/60 and 5/60 of the length of the latter) and the same applies to the second engagement means 5a, 5b with respect to the screw 2, whereby for the purpose of identifying the distance indicated above, a central or median part of the engagement means relative to the longitudinal development direction of the screw 2 and stem 3 will be taken as reference.

According to a less preferred variant, the first or second engagement means (in particular, when they comprise a respective threaded section) extend substantially for the entire length of the respective element 3 or 2, if desired for about 90% of this length. In this case, this does not occur simultaneously for both the first and the second engagement means.

The axial seat AS crosses the rear end or back 2b and preferably develops up to the front end or tip 2a, although it may or may not cross the latter.

With reference to the non-limiting embodiment illustrated in the figures, the first engagement means comprise at least an externally threaded section 4b of the stem or pin 3, while the second engagement means comprise at least an internally threaded section or nut screw 5b of the tubular component or cannulated screw 2 for screwing engagement with the at least internally threaded section 4b.

Advantageously, the first engagement means comprise a conical or frusto-conical section 4a externally delimited on the stem or pin 3, while the second engagement means comprise a conical or frusto-conical seat 5a internally delimited by the cannulated screw 2 for fitting engagement of the conical or frusto-conical section externally 4a delimited on the stem or pin 3.

More specifically, according to the non-limiting embodiment illustrated in the figures, in FIGS. 1 to 3, the first engagement means comprise a conical or frusto-conical section 4a and an externally threaded section 4b externally delimited on the stem or pin 3, in particular one 4a at the tip and the other 4b at the back, while the second engagement means comprise a conical or frusto-conical seat 5a internally delimited in the cannulated screw 2, in particular at the tip 2a for fitting engagement of the conical or frusto-conical section 4a externally delimited on the stem or pin 3 and an internally threaded section 5b, optionally on the back, of the cannulated screw 2 for screwing engagement of the externally threaded section 4b.

Figure 4:
FIG. 4 is another embodiment of a stem or pin for a device according to the present invention.

FIG. 4 instead illustrates a stem or pin 3 with a first conical or frusto-conical section 4a externally delimited at a zone Z1, if desired at the tip, on the stem or pin 3 as well as a second conical or frusto-conical section 4c externally delimited at a zone Z2, if desired at the back, on the stem or pin 3. Clearly, such a stem or pin 3 would be insertable and engageable with a cannulated screw with two conical or frusto-conical seats 5a each internally delimited at an area A1, A2 in cannulated screw 2, for example one on the tip and the other on the back.

As regards the graft tubular component or the cannulated screw 2 in more detail, it can comprise an elongated body, which advantageously has externally a thread 6 at an end or tip 2a, which thread 6 is provided to facilitate insertion of the tubular component or screw 2 in bone B or tissues.

The elongated body can then have a substantially smooth external surface at its other external sections, so that, for example, when the screw 2 is fitted in a fractured bone B, the smooth external surface is in proximity to the fracture gap F, in which case the absence of the thread 6 in this area would allow the development of micro-movements and would favor the correct formation of the callus during the postoperative period.

The elongated body of the screw 2 develops along a longitudinal axis and defines the axial seat AS, the latter also extending along the same longitudinal axis.

The front end or tip 2a of the cannulated screw 2 can be substantially tapered and/or with a suitable shape that allows its insertion into the soft tissue, first, and then into the bone tissue of the patient.

Moreover, a notch 7 may be provided at the front end or tip 2a, which is designed to allow a better insertion of the screw 2 in the tissues to be crossed by the screw.

On the other hand, as regards the rear end or back 2b of the cannulated screw 2, it can define an engagement portion, for example with a hexagonal shape or with another suitable shape, designed to allow the screw 2 to be connected using an insertion tool, such as explained below.

Clearly, the engagement portion can be positioned in a seat recessed in the back 2b or protrude with respect to it.

The screw 2 can have any configuration, for example with cylindrical or prismatic section or with a cross section having another configuration.

Moreover, the screw 2 can have any suitable dimensions, for example a diameter between 6 mm and 12 mm and a length between 70 mm and 120 mm.

Figure 5:
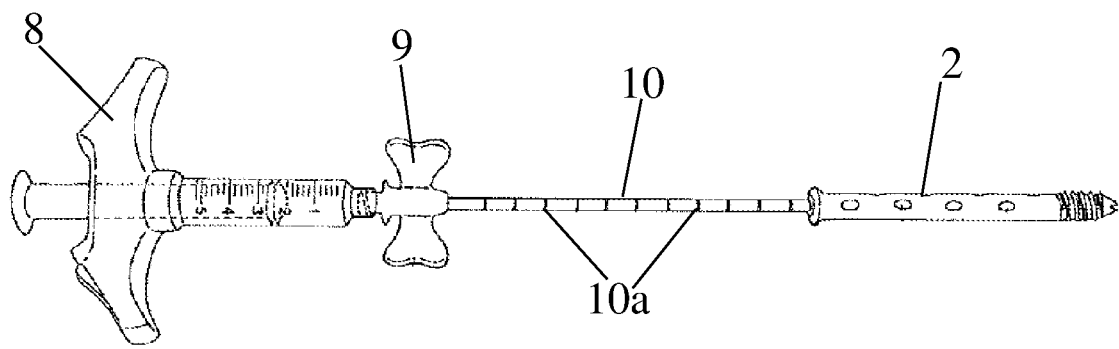
FIG. 5 is a schematic view illustrating a device according to the present invention grafted in an area of a patient.
Figure 6:
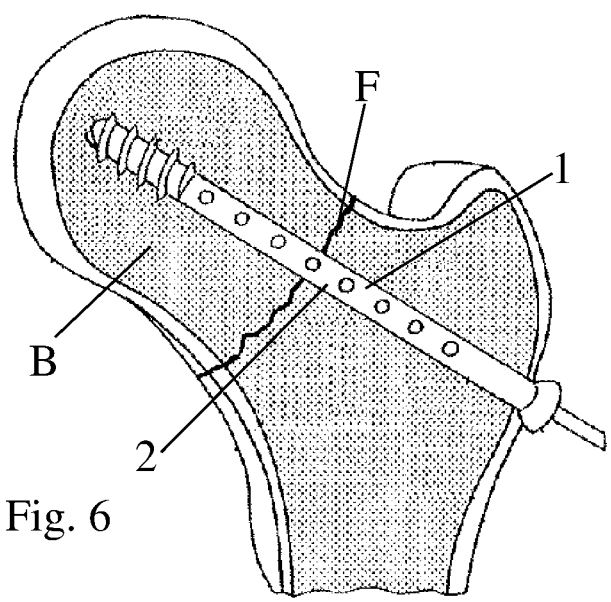
FIG. 6 is a side view of a kit according to the present invention with injection system and connectable injector.

As illustrated in FIG. 5, the device 1 can be coupled to an injection system 8, through coupling means 9 of a known type as well as through an injector 10, as better explained below.

Through the injection system 8 and the device 1 the injection takes place, in the site of interest, for example of bone cement, for example containing polymethyl methacrylate and/or regenerative factors, for example stem cells, growth factors, platelet gel and/or other antibiotic or medicinal substances, in order to stabilize, cure and possibly regenerate the fractures of patients who have suffered a trauma or of osteoporotic patients.

With regard in particular to the stem or pin 3, as partly indicated, it has a conformation substantially elongated and parallel to the axis of the screw or tubular component 2. This component 3 is able to ensure greater resistance of the implant, in particular owing to the presence of engagement means as described above.

The pin 3 can have a length substantially equal to that of the axial channel or seat AS.

The pin 3 is inserted into the axial channel or seat AS of the screw 2, at the end of the injection of the substances indicated above, using a special insertion tool, possibly in the shape of a screwdriver. The insertion of the pin 3 in the channel AS determines the emptying of the latter by the bone cement and/or the injected substances, which allows to obtain a precise measurement of the quantity of cement and/or substances injected since the quantity measured by the injection system 8 corresponds to the one actually injected into the screw 2 insertion site.

Furthermore, the emptying of the channel AS by the pin 3 renders it possible to make the channel available for any further injections of substances or for the subsequent prescribed surgical procedure.

The diameter of the pin 3 is slightly smaller than the diameter of the channel AS where it is inserted, but the diameter of the pin 3 is such as to substantially close such channel.

As regards in particular the holes or slots HS1, HS2, they are clearly in fluid communication with the axial seat AS and arranged in such a way as to allow the injection of the bone cement and/or the aforementioned substances selectively through the desired holes or slots HS1, HS2 starting from the axial seat. In particular, the holes or slots HS1, HS2 can be in various shapes, positions and size, in order to allow a "targeted" introduction of the above indicated substances, if desired.

If desired, according to the embodiments illustrated in the figures, the holes or slots can comprise holes or slots, for example with circular section HS1, delimited between any coils of the thread 6 and suitable for ensuring a homogeneous distribution of the substances, and holes or slots HS2, for example with an elliptical section or delimited in the other portions of the screw or tubular component 2 and suitable for ensuring a large flow rate of fluid to be delivered into the body.

Preferably, the holes HS1, HS2 are arranged substantially along the entire surface of the elongated body of the tubular component or screw 2, so that it is possible to carry out, through the screw 2 itself, a selective injection of the substances listed above in any desired or necessary position.

The stem or pin 3 can be made of any suitable material, for example titanium or its alloys.

Clearly, the introduction of the pin 3 ensures the closure of the screw 2 and further enhances the resistance of the device 1, transforming a cannulated section, such as the screw 2, into a solid section, given by the stem or pin 3 inserted in the screw 2, and partially removing the cut effects given by the presence of the holes or slots HS1, HS2.

Subject-matter of the present invention is also a kit for the selective biological synthesis of a bone tissue comprising a device 1 as well as an injection system 8 and an injector 10 connectable on one side to the injection system 8 and on the other to the cannulated screw 2.

If the device 1 is to be grafted, one proceeds first inserting a guide wire and then preparing the operating site on the cortical part of bone B by mounting a cutter on the guide wire, extraction of the cutter and reduction of the fracture F.

Next, the implantation technique involves mounting
    a measuring device on the guide wire, in order to identify
        the correct length for the tubular component or screw 2,
    the screw 2 on a special first insertion tool, for example
        a screwdriver or other tools suitable for the purpose,
    the first insertion tool and the screw 2 on the guide wire
        and then carry out the consequent screwing of the same,
        by rotating the insertion tool.

The insertion tool can have a handle, for example a hollow rod, designed to allow the guide wire and other devices and/or accessories necessary in the subsequent phases of the implant to pass through it, and a complementary tip to the engagement section present in the second end or head 2b of the screw 2, so as to allow the same to be screwed.

Once screw 2 has been inserted and/or screwed in, the guide wire is extracted, and the same applies to the handle of the first insertion tool. The rod of the first insertion tool, on the other hand, is left in place for its subsequent use.

In a subsequent phase, the preparation and assembly of the injection system 8 takes place, possibly in the form of a syringe, into which the above-mentioned substances, such as bone cement and/or regenerative factors and/or stem cells and/or growth factors and/or platelet gel and/or other antibiotic or medicinal substances, etc., are inserted.

As indicated above, the device 1 further comprises an injector 10, if desired of a cannulated type, comprising a lower end, capable of being coupled with the injection system 8, possibly by means of an adapter 9 of a known type, and an upper end, through which the aforesaid substances are injected, suitable for being inserted into the seat or channel AS of the screw 2.

The injector 10 allows to obtain a selective injection of the aforementioned substances through the necessary/desired holes or slots HS1, HS2 and/or through the first end or tip 2a of the screw 2.

This injector 10 is inserted inside the longitudinal channel AS of the screw 2. More specifically, this injector 10 can be completely inserted into the longitudinal channel AS of the screw 2, allowing the sections of the screw 2 corresponding to its first end or tip 2a to be reached.

The injector 10 can then have a series of graduated references 10a, which allow it to be aligned with the base of the first insertion tool and consequently with the tip 2a of the tubular component or screw 2. These references make it possible to identify and reach the desired or necessary holes or slots HS1, HS2.

After inserting the injector 10 on the previously filled injection system and before inserting the injector 10 itself inside the rod of the insertion tool, the injector 10 is filled with the substances contained in the injection system 8.

Once the injector 10 has been inserted inside the rod of the insertion tool, the graduated references 10a, if provided, of the injector 10, and therefore of its upper end, are aligned with the base of the insertion tool, in order to identify and select the position of the various holes or slots HS1, HS2 to be perfused, according to the depth to be reached with the upper end of the injector itself or the operative strategy being followed.

To obtain a homogeneous injection along the entire elongated body of the screw 2, it is necessary to start the injection from the distal part of the screw 2, at its first end or tip 2a.

Once the injection has been completed in the desired points, the implantation technique involves detaching the injection system 8 from the injector 10, still in place, and inserting, inside the injector itself, an emptying device (not shown), so as to completely empty the body of the injector 10 and avoid the loss of bone cement and/or regenerative factors and/or other substances in the soft tissues or inside the rod of the first insertion tool.

The emptying device can have a plunger or pin shape or any other shape suitable for the purpose.

Once the injector 10 has been extracted together with the emptying device, the pin 3 is mounted in a special second insertion tool and everything is inserted inside the first insertion tool left in place. The pin 3 is inserted and/or screwed through the rotation of the second insertion tool by coupling the removable engagement means located in two areas A1, A2, if desired in the tip and in the back of the stem or pin 3.

Once the pin 3 has been inserted and/or screwed in, the first and second insertion tools are extracted.

Thanks to the insertion of the pin 3, the screw 2 is left free from residues of bone cement and/or other substances and this allows—during the revision—to remove the pin 3 and carry out new injections if required or periodic reviews of the therapeutic strategy through repeatable, selective and minimally traumatic surgical accesses. Therefore, the screw 2 has a removable closure by the pin 3.

During surgery it is advisable to implant at least two screws with parallel direction, one above and one below, with a distance of about 17 mm from each other, to improve the overall hold of the device 1 on the bone and to avoid, should the second screw not be used, the rotation of the detached bone segment on the axis of the first screw.

As it will be possible to ascertain, in accordance with the present invention, the introduction of the pin 3 guarantees the closure of the screw 2 and further enhances the resistance of the device 1, transforming a cannulated section, such as the screw 2, into a solid section, given by the stem or pin 3 inserted in the screw 2, and partially removing the cut effects due to the presence of the holes or slots HS1, HS2.

In this regard, the provision of engagement means in different and distant zones/areas, and advantageously at both the tip and the back of the screw 2 and of the stem 3 clearly improves the stability to deformation and the resistance to shear forces compared to the above proposed solutions.

Moreover, the presence of engagement means at the tip prevents or reduces the possibility of reflux of biological or other fluids into the tip of the cannulated screw.

In addition, thanks to the present invention, a full screw is actually obtained from a cannulated screw, which allows a patient to obtain again the original functional performance, such as loading in particular, in a short time after surgery.

Changes and variants of the invention are possible within the scope defined by the claims.

The invention claimed is:

1. Device A device for the selective biological synthesis of a bone tissue arranged to allow the stabilization of a fracture or an osteoporotic bone tissue and including a graft tubular component or cannulated screw defining an axial channel or seat as well as at least one hole or slot transversal to said axial channel or seat and in fluid communication with the latter, said device further comprising a stem or pin housable within said axial channel or seat, said stem or pin having first removable engagement means externally to said stem or pin, while said graft tubular component or cannulated screw comprises second removable engagement means in said axial channel or seat arranged to removably engage said first engagement means, wherein said first engagement means extend at at least two zones of said stem or pin at a distance from each other, while said second engagement means extend at at least two areas of said tubular component or cannulated screw at a distance among them equal to the distance between said two zones of said first engagement means, so that the first engagement means engage at each extension zone a respective extension area of the second engagement means, wherein said first engagement means comprise an externally threaded section of said stem or pin, while said second engagement means comprise an internally threaded section of said tubular component or cannulated screw for the screwing engagement of said externally threaded section, and wherein said first engagement means comprise a conical or frusto-conical section externally delimited on said stem or pin, while said second engagement means comprise a conical or frusto-conical seat internally delimited by said tubular component or cannulated screw for the fitting engagement of said conical or frusto-conical section externally delimited on said stem or pin.

2. The device according to claim 1, wherein said two zones are at a distance from each other equal to at least half the length of said stem or pin.

3. The device according to claim 1, wherein said two zones are at a distance from each other equal to at least 70% of the length of the stem or pin.

4. The device according to claim 1, wherein said two areas are one at the front end or tip of said tubular component or cannulated screw and the other at the rear end or back of said tubular component or cannulated screw.

5. The device according to claim 1, wherein said two areas are one at the front end or tip of said tubular component or cannulated screw and the other at the rear end or back of said tubular component or cannulated screw, wherein said externally threaded section is provided at the back of said stem or pin, while said internally threaded section is provided at the back of said tubular component or cannulated screw, and wherein said conical or frusto-conical section is externally delimited on the tip of said stem or pin, while said conical or frusto-conical seat is internally delimited on the tip of said tubular component or cannulated screw.

6. The device according to claim 1, wherein said tubular component or cannulated screw delimits a plurality of holes or slots transversal to said axial seat distributed along the length of said cannulated screw.

7. A kit for the selective biological synthesis of a bone tissue comprising the device according to claim 1 as well as an injection system and an injector connectable on one side to the injection system and on the other to said tubular component or cannulated screw for the selective injection of substances through said at least one hole or slot and/or through a first end or tip of said tubular component or cannulated screw.

8. A device for the selective biological synthesis of a bone tissue arranged to allow the stabilization of a fracture or an osteoporotic bone tissue and including a graft tubular component or cannulated screw defining an axial channel or seat as well as at least one hole or slot transversal to said axial channel or seat and in fluid communication with the latter, said device further comprising a stem or pin housable within said axial channel or seat, said stem or pin having first removable engagement means externally to said stem or pin, while said graft tubular component or cannulated screw comprises second removable engagement means in said axial channel or seat arranged to removably engage said first engagement means, wherein said first engagement means extend at at least two zones of said stem or pin at a distance from each other, while said second engagement means extend at at least two areas of said tubular component or cannulated screw at a distance among them equal to the distance between said two zones of said first engagement means, so that the first engagement means engage at each extension zone a respective extension area of the second engagement means,
wherein said first engagement means comprise a first conical or frusto-conical section externally delimited at a zone on the stem or pin as well as a second conical or frusto-conical section externally delimited at an another zone on the stem or pin, while said second engagement means comprise a first conical or frusto-conical seat internally delimited by said tubular component or cannulated screw for the fitting engagement of said first conical or frusto-conical section and a second conical or frusto-conical seat internally delimited by said tubular component or cannulated screw for the fitting engagement of said second conical or frusto-conical section.

9. The device according to claim 8, wherein said two zones are at a distance from each other equal to at least half the length of said stem or pin.

10. The device according to claim 8, wherein said two zones are at a distance from each other equal to at least 70% or 80% or 90% of the length of the stem or pin.

11. The device according to claim 8, wherein said two areas are one at the front end or tip of said tubular component or cannulated screw and the other at the rear end or back of said tubular component or cannulated screw.

12. The device according to claim 8, wherein said tubular component or cannulated screw delimits a plurality of holes or slots transversal to said axial seat distributed along the length of said cannulated screw.

13. A kit for the selective biological synthesis of a bone tissue comprising the device according to claim 8 as well as an injection system and an injector connectable on one side to the injection system and on the other to said tubular component or cannulated screw for the selective injection of substances through said at least one hole or slot and/or through a first end or tip of said tubular component or cannulated screw.

* * * * *